United States Patent
Weinstock et al.

(10) Patent No.: US 11,241,686 B2
(45) Date of Patent: Feb. 8, 2022

(54) SEPARATOR

(71) Applicant: SARSTEDT AKTIENGESELLSCHAFT & CO.KG, Nümbrecht (DE)

(72) Inventors: Mark Weinstock, Helmenzen (DE); Christian Wegener, Nümbrecht (DE); Ulrich Karrenberg, Marienheide (DE)

(73) Assignee: SARSTEDT AKTIENGESELLSCHAFT & CO.KG, Nümbrecht (DE)

( * ) Notice: Subject to any disclaimer, the term of this patent is extended or adjusted under 35 U.S.C. 154(b) by 130 days.

(21) Appl. No.: 16/608,798

(22) PCT Filed: Apr. 25, 2018

(86) PCT No.: PCT/EP2018/060597
§ 371 (c)(1),
(2) Date: Oct. 25, 2019

(87) PCT Pub. No.: WO2018/197562
PCT Pub. Date: Nov. 1, 2018

(65) Prior Publication Data
US 2021/0106989 A1  Apr. 15, 2021

(30) Foreign Application Priority Data
Apr. 26, 2017  (DE) ............... 10 2017 108 933.0

(51) Int. Cl.
*B01L 3/00* (2006.01)
*A61B 5/15* (2006.01)
*G01N 33/49* (2006.01)

(52) U.S. Cl.
CPC .... *B01L 3/50215* (2013.01); *A61B 5/150755* (2013.01); *G01N 33/491* (2013.01)

(58) Field of Classification Search
CPC .......... A61B 5/15003; A61B 5/150755; B01L 3/50215; G01N 33/491; A01K 93/00; A01K 93/02
See application file for complete search history.

(56) References Cited

U.S. PATENT DOCUMENTS

| | | |
|---|---|---|
| 3,887,464 A | 6/1975 | Ayres |
| 4,088,582 A | 5/1978 | Murty et al. |
| 4,443,345 A | 4/1984 | Wells |
| 4,843,869 A | 7/1989 | Levine et al. |

(Continued)

FOREIGN PATENT DOCUMENTS

| | | |
|---|---|---|
| DE | 60023823 | 8/2006 |
| DE | 69931584 | 5/2007 |

(Continued)

*Primary Examiner* — Terry K Cecil
(74) *Attorney, Agent, or Firm* — Smartpat PLC

(57) ABSTRACT

A separator for separating a first from a second phase of a liquid in a tubular container has an elastic float with a circular sealing edge for sealing engagement with the inside of the tubular container in a sealing position. At the underside of the float, a ballast is attached. The density of the ballast is greater than the density of the float and the density of the entire separator is in a range between the density of the first phase and the density of the second phase of the liquid. The float has a local constriction and, in the area of the constriction, a membrane.

18 Claims, 6 Drawing Sheets

(56) References Cited

U.S. PATENT DOCUMENTS

| | | | |
|---|---|---|---|
| 5,632,905 A | 5/1997 | Haynes | |
| 6,280,400 B1 | 8/2001 | Niermann | |
| 6,406,671 B1 | 6/2002 | DiCesare et al. | |
| 6,409,528 B1 | 6/2002 | Bodnar | |
| 6,479,298 B1 * | 11/2002 | Miller | B01L 3/50215 210/121 |
| 6,537,503 B1 | 3/2003 | Conway | |
| 7,188,734 B2 | 3/2007 | Konrad | |
| 8,998,000 B2 * | 4/2015 | Crawford | B01L 3/50215 210/512.1 |
| 9,333,445 B2 | 5/2016 | Battles et al. | |
| 9,333,455 B2 | 5/2016 | Gil | |
| 9,364,828 B2 | 6/2016 | Crawford et al. | |
| 9,731,290 B2 | 8/2017 | Crawford et al. | |
| 9,919,307 B2 | 3/2018 | Crawford et al. | |
| 9,919,308 B2 | 3/2018 | Crawford et al. | |
| 10,376,879 B2 | 8/2019 | Crawford et al. | |
| 10,413,898 B2 | 9/2019 | Crawford et al. | |
| 10,456,782 B2 | 10/2019 | Crawford et al. | |
| 10,807,088 B2 | 10/2020 | Crawford et al. | |
| 2002/0094305 A1 | 7/2002 | DiCesare et al. | |
| 2002/0132367 A1 | 9/2002 | Miller et al. | |
| 2002/0156439 A1 | 10/2002 | Iskra | |
| 2004/0256331 A1 | 12/2004 | Arking et al. | |
| 2005/0059163 A1 | 3/2005 | Dastane et al. | |
| 2010/0288694 A1 | 11/2010 | Crawford et al. | |
| 2011/0036786 A1 | 2/2011 | Ellsworth | |
| 2013/0315798 A1 | 11/2013 | Crawford et al. | |
| 2016/0136640 A1 | 5/2016 | Losada et al. | |

FOREIGN PATENT DOCUMENTS

| | | |
|---|---|---|
| EP | 0017127 A2 | 10/1980 |
| EP | 0098150 A2 | 1/1984 |
| EP | 0753741 A1 | 1/1997 |
| EP | 1106252 A2 | 6/2001 |
| JP | H09222427 A | 8/1997 |
| WO | 2009073232 A1 | 6/2009 |
| WO | 2010132783 A1 | 11/2010 |
| WO | 2014120678 A2 | 8/2014 |
| WO | 2016076911 A1 | 5/2016 |

* cited by examiner

SEPARATOR

TECHNICAL FIELD

The invention relates to a separator for separating a first from a second phase of a liquid in a tubular container. In particular, separators are meant to separate blood serum being the first phase from cruor being the second phase in blood being the liquid within a blood collection tube.

BACKGROUND

Blood collection tubes having separators are generally known in the prior art. In a delivery state the separators are fixed in an initial position of the blood collection tubes. When blood flows into the blood collection tube via an inlet, it flows around or through the separator; in any case, in the initial position, the separator does not constitute a seal for the blood within the blood collection tube. For medical analysis it is necessary for the blood to be separated into two components, namely blood serum and cruor. For this purpose, the blood collection tube with the blood located therein is centrifuged. The heavier cruor then settles due to centrifugation in the area near the bottom of the blood collection tube, while the lighter blood serum floats on the cruor. The separator detaches from its initial position and moves into a sealing position under the action of the centrifugal force. Because the density of the entire separator lies in a value range between the density of the blood serum and the density of the cruor, the separator automatically positions itself exactly at the phase boundary between blood serum and cruor. This position is also referred to as sealing position, because in this position, the separator rests with its sealing edge circumferentially against the inner side of the tubular sample tube in a sealing manner and thus cleanly separates the blood serum from the cruor. The separator maintains this sealing position even after the end of centrifugation so that the blood serum and the cruor are separately available for a laboratory examination.

Separators are disclosed, for example, in international patent application WO 2010/132783 A1. The separators described therein each have a float made of elastic material having a sealing edge that is circularly circumferential in top view for resting against the inner side of a tubular sample container in a sealing manner in the sealing position. A ballast is fastened in each case to the underside of the float. The density of the ballast is in each case greater than the density of the float and the density of the entire separator lies in a value range between the density of the first phase and the density of the second phase of the liquid.

The prior art in the form of document WO 2016/076911 A1 discloses a separation unit for separating a liquid into a first light phase and a second heavier phase using centrifugal force, wherein the liquid can be blood. A tubular container has a separator, wherein the separator has a float in the upper area and a ballast in the lower area. The separator is designed for resting against the inner side of the tubular container in a sealing manner. The density of the ballast in this case is greater than the density of the float and the density of the separator lies between the density of the first phase and the density of the second phase of the liquid to be separated.

Document DE 699 31 584 T2 describes a device for separating a fluid sample under centrifugal force into a phase having a higher specific gravity and a phase having a lower specific gravity, wherein the fluid sample can be a blood sample. The device has a separator element (separator) which is arranged in a cylindrical tube. The separator element has a float in the upper area and a ballast element in the lower area and a sealing body resting against the inner side of the tube in a sealing manner. The density of the ballast in this case is greater than the density of the float and the entire density of the separator lies between the density of the first phase and the density of the second phase of the liquid to be separated.

Document DE 600 23 823 T2 includes a device for separating a liquid sample (for example, blood) into a first phase of high density and into a phase of low density under the action of centrifugal force. A separator is arranged in a tube having a cylindrical side wall, which separator has a float in the upper area and a ballast part in the lower area and a bellows for resting against the inner side of the tube in a sealing manner. The density of the ballast part in this case is greater than the density of the float and the entire density of the separator lies between the densities of the first phase and the second phase of the liquid to be separated. The float includes a "narrow neck", i.e. a local constriction, between the upper and lower end.

SUMMARY

The invention has the object to propose an alternative separator.

This object is solved by the subject matter as claimed. The separator is characterized in that its float has a constriction and has a membrane in the area of the constriction.

The claimed membrane has two functions: First, it seals the float in the area of its constriction against the liquid; thus, a flow of the liquid through the float and also through the entire separator is effectively prevented. On the other hand, the membrane acts as a tension spring insofar as it counteracts a pulling force acting on the separator, in particular centrifugal force, which pulls the float and the ballast apart in the liquid relative to one another and thus thins the separating body. The thinning is necessary so that the separator, when it moves under the influence of centrifugal force from its initial position to the sealing position, does not get struck inside the tubular container. When the traction force or the centrifugal force is reduced or switched off, the float and the ballast body are returned to their original spacing, also due to the spring force of the membrane, as a result of which the separator widens again in the sealing position. A result of the widening is that the sealing edge of the float rests with sufficient pressure circumferentially sealingly on the inside of the tubular container.

The described required spring action of the float can be realized more easily with a thin membrane than with a voluminous solid body, because the membrane can be stretched more easily. Furthermore, it is advantageous that the thin membrane requires little material. However, the membrane hardly acts as a floating or buoyant body. This function is performed by the part of the float which surrounds the membrane.

Unless otherwise stated, the separator is described in the following in a normal position. The ballast is arranged below the float in this normal position. The center of gravity of the float, the center of gravity of the ballast and the center of gravity of the entire separator all lie on a vertical line. The terms used in the following, such as vertical, horizontal, below, side view and top view, etc., all refer to this normal position. The sealing position corresponds to the normal position where the tubular container is vertical.

The term local constriction means a local taper or reduction of cross-sectional area. In the area of its constriction the float is reduced to the membrane.

According to a first embodiment, the membrane is either elastic and/or, at least in the unloaded state, formed wave-shaped with wave crests and wave troughs. This design of the membrane advantageously enables said spring action of the membrane.

The wave crests and the wave troughs of the membrane can each be annular; the membrane then possibly develops tensile forces in the radial direction relative to its center. Alternatively, the wave troughs and the wave crests of the membrane can also be designed in each case in a straight line and parallel to one another; the membrane then unfolds said tensile forces, in particular in a direction perpendicular to the wave crests and troughs.

From a manufacturing point of view, it is advantageous if the membrane is made of the same material as the float, more preferably even formed as one piece with the float. The float is then very easy to produce, especially as an injection molded part.

The float may be spherical or cup-shaped; however, it is important that its outer contour, when viewed from the side, deviates from a circular shape, at least from one viewing direction. This is important, so that the separator in its initial position, i.e. at delivery, is not completely sealingly applied to the inside of the tubular container in the circumferential direction, but that the inflowing liquid, in particular blood, can flow past the separator into lower volume areas of the tubular container.

Overall, the surface contour of the float is selected such that liquid, in particular blood, which in particular wets the area of the constriction or of the membrane, can flow into the container.

The circumferential sealing edge formed on the float can—viewed in the side view—be formed to extend in a wave-shaped manner; this offers the advantage that the sealing edge can be formed extending around the constriction at least in sections. Alternatively, the sealing edge can also—viewed in a side view—extend rectilinear or horizontally; it is then typically arranged above the constriction.

The float may have a local elevation or a local flattening or bead on its upper side facing away from the ballast. Both alternative embodiments contribute to the fact that the contour of the separator and in particular of the float deviates, in a side view, from the pure circular shape. Consequently, as stated, this enables a flow of liquid around the separator, in particular in its initial position. Thus, it is particularly advantageously ensured that liquid residues, for example blood residues, flow off and do not accumulate there.

Finally, the ballast can be made of a material which is less elastic than the material of the float or the material of the membrane. This is true because the said sealing edge is typically attached to the float and not to the ballast. For the function of the separator, it is important that the sealing edge under the action of centrifugal force on the float—and thus on the sealing edge—is elastically deformable to allow liquid to flow around the separator within the tubular container. If the sealing edge is not attached on the ballast, this elasticity is not required of the ballast; the ballast can therefore be less elastic.

In all embodiments of the separator, the surface of the ballast may in each case have a predetermined static friction coefficient or the ballast may have an adhesive element which has on its surface the predetermined static friction coefficient. The static friction coefficient is predetermined in such a way that the separator only releases from its initial position within the tubular container if a force, in particular a centrifugal force, which is greater than a predetermined force threshold, acts on it.

DETAILED DESCRIPTION

Figure 1:
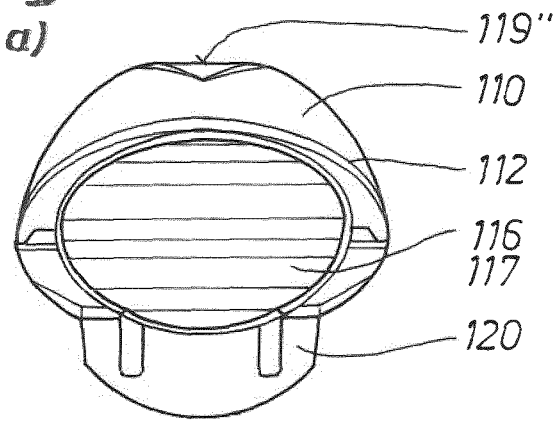
FIGS. 1a and 1b show a separator with a membrane according to a first embodiment in a side view and a perspective view.
Figure 1:
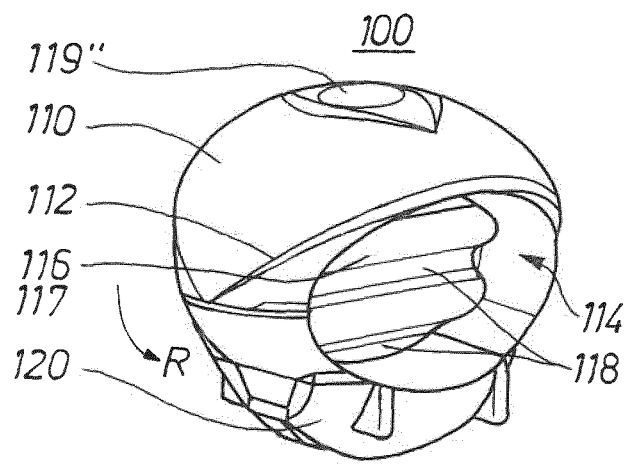

The invention is described in detail in the following with reference to said figures in the form of exemplary embodiments. The same technical elements are designated by the same reference numerals in all figures.

FIGS. 1a and 1b show the separator 100 in a spherical configuration. It consists of an elastic float 110 with a circular sealing edge 112 (in plan view). This does not preclude that the sealing edge 112 is formed wave-shaped in the side view. At the underside of the float 110, a ballast 120 is attached.

The density of the ballast 120 is greater than the density of the float 110 and the density of the entire separator 100 is in a range of values between the density of the first phase and the density of the second phase of the liquid. The density of the second phase of the liquid is greater than the density of the first phase of the liquid. For blood as a fluid, this means that the cruor as the second phase has a greater density than the blood serum, which corresponds to the first phase.

According to FIGS. 1a and 1b, the float 110 is locally constricted. In the area of the constriction 114, it is designed as a membrane 116. The membrane is wave-shaped with wave crests 117 and wave troughs 118. Additionally or alternatively, the membrane 116 could also be formed of elastic material. The design of the membrane in wave shape and/or of elastic material is required to enable the above-described spring effect of the membrane.

In the exemplary embodiment shown in FIGS. 1a and 1b, the wave troughs 118 and the wave crests 117 of the membrane 116 each extend in a straight line and parallel to each other (1st variant). The membrane therefore generates its spring effect in the arrangement of FIG. 1a in the vertical direction. At its upper side opposite the ballast 120, the float 110 has a local flattening or bead 119"; this allows the fluid to locally flow around the separator also in its initial position 210 within the tubular container. As shown in FIGS. 1a and 1b—viewed in side view—the sealing edge 112 which extends in the circumferential direction R is wave-shaped and is at least partially guided around the edge of the local constriction 114.

Figure 2:
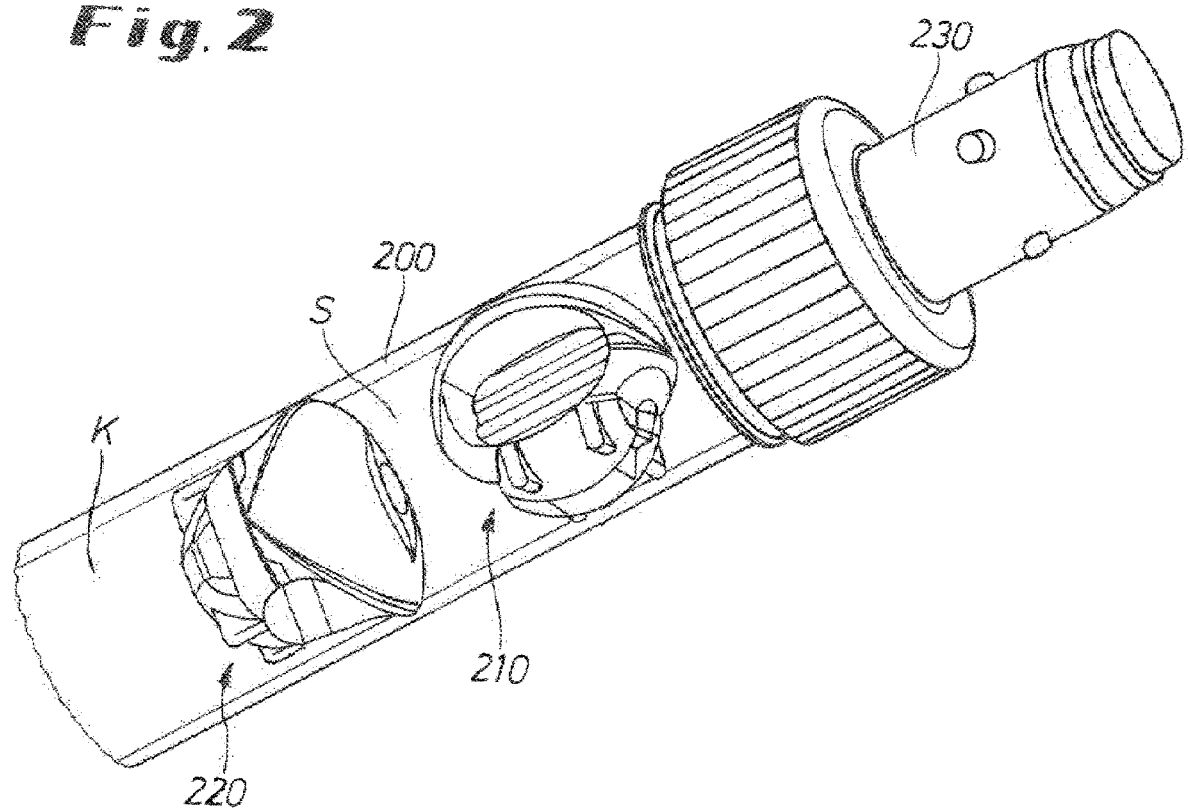
FIG. 2 shows the separator of FIG. 1a in a tubular container.

FIG. 2 shows the separator 100 within the tubular container 200. The tubular container is, for example, a tube for taking blood. In the delivery state of this tubular container 200, the separator 100 is releasably clamped in an initial position 210. It is there arranged transverse in the container.

Due to its not perfectly circular outer contour (in side view from the direction of the inlet 230 of the liquid), the liquid, in particular blood, flows around the separator in this initial position but does not flow through it. The blood flowing into the container can thus also flow into deeper volume regions of the container located below the separator.

Under the action of a force in the longitudinal direction of the tubular container, in particular a centrifugal force, the separator 100 is released from its initial position and moves into said sealing position 220. During centrifugation, the first phase, for example blood serum S, is separated from the second phase, for example cruor K, and the separator 100, due to its density, positions itself exactly on the border between these two phases of the liquid. The movement of the separator from its initial position into the sealing position is further facilitated by the fact that the separator stretches slightly in the vertical direction and thins under the action of the centrifugal force. Thus, during centrifugation and during said migration of the separator its sealing edge is not circumferentially tight against the inside of the tubular container. During its migration from the initial position to the sealing position, the separator rotates by 90°. Only after completion of the centrifugation, i.e. in the sealing position 220, does the separator relax again. This means that also due to the tensile force of the membrane, the float and the ballast are brought a little closer to one another, with the result that the separator widens, so that the sealing edge 112 is circumferentially in contact with the inside of the tubular container 200 and in this sealing position separates the first phase of the liquid from the second phase.

Figure 3:
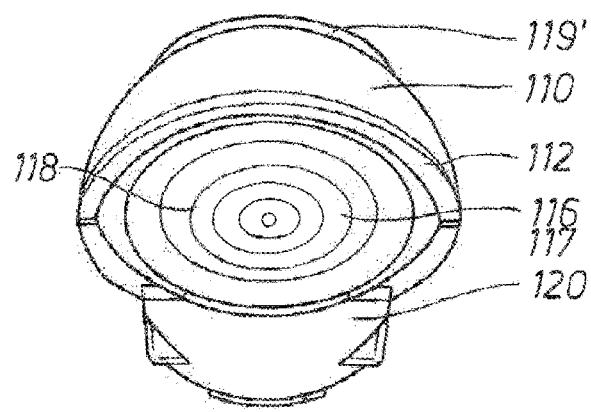
FIGS. 3a to 3d show the separator with the membrane according to a second embodiment.
Figure 3:
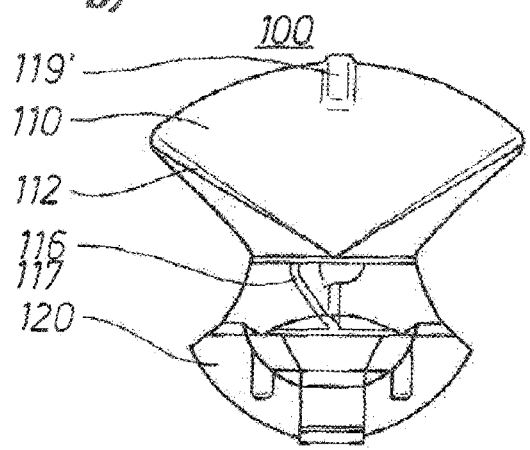
Figure 3:
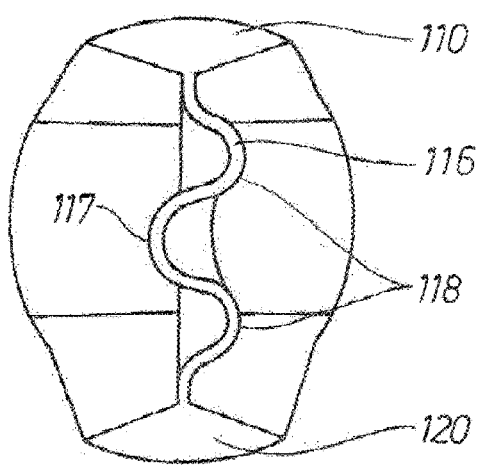
Figure 3:
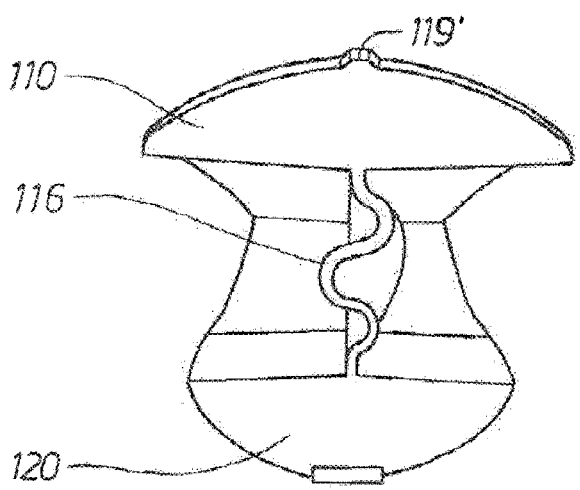

FIG. 3 shows the separator in an alternative embodiment. Specifically, FIGS. 3a and 3b each show this embodiment in a side view, but from different viewing directions which are offset by 90°. FIGS. 3c and 3d show the separator in the side view according to FIG. 3b, though not in a perspective view, but in longitudinal sections at different depths. The spherical separator of FIG. 3 differs from the spherical separator of FIG. 1a, on the one hand in the shape of the membrane 116 and on the other hand in the design of the upper side of the float. The wave crests 117 and the wave troughs 118 of the membrane are not straight in this case, but annular and essentially coaxial with one another (second variant). This offers the advantage that the spring action of this membrane is not one-dimensional, but two-dimensional, namely radially to the center of the membrane. Unlike the separator according to FIG. 1a, the separator 100 according to FIG. 3 does not show any flattening on the surface of the float, but rather a local elevation 119'. With this local elevation, the separator 100 rests against the inside of the tubular container 200 in the initial position 210. Because of this local elevation 119', the outer contour of the separator and in particular of the float 110 deviates from a perfect circular shape; this contributes advantageously to the fact that the separator with the surface of the float does not contact the inside of the tubular container in this area in a sealing manner, but instead the liquid can flow around it there as well.

Figure 4:
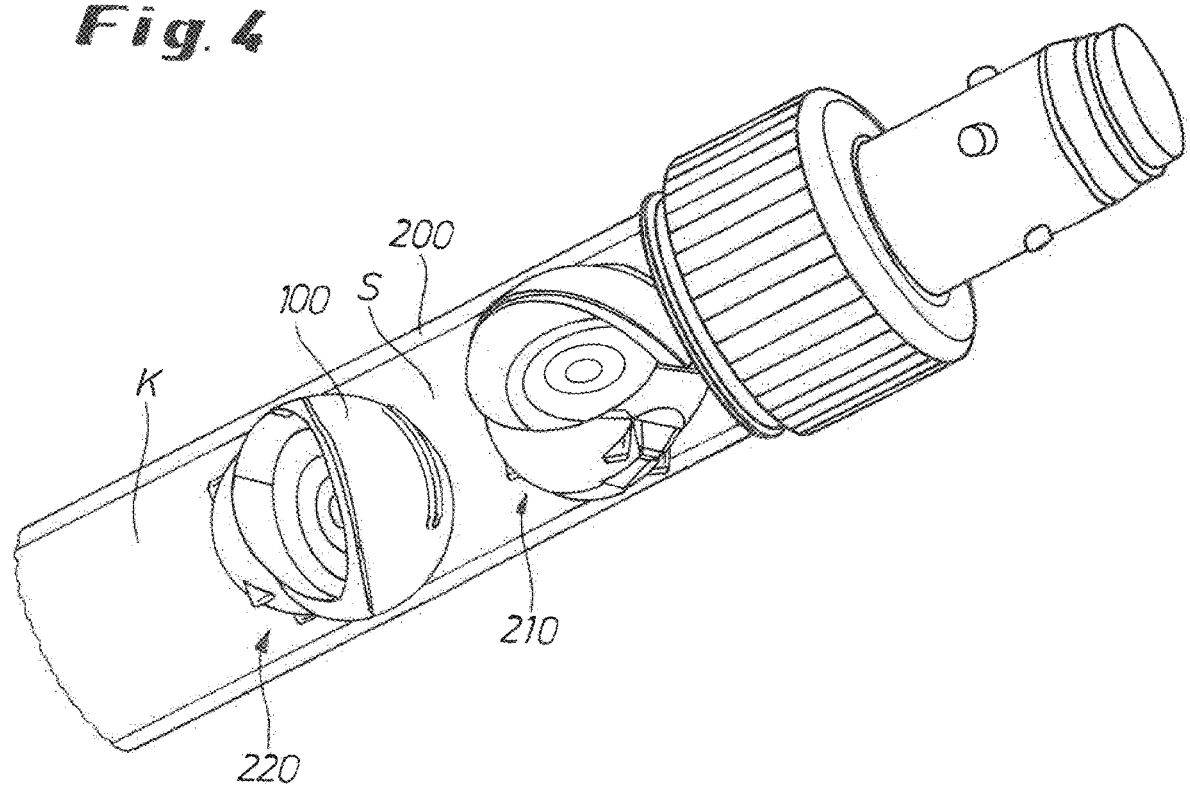
FIG. 4 shows the separator of FIG. 3 in the tubular container.

FIG. 4 shows the tubular container 200 with the separator 100 according to FIG. 3. As said, in the initial position 210, the separator 100 rests against the inside of the container 200, in particular with the local elevation 119'. Otherwise, regarding FIG. 4 reference is made to the description of FIG. 2, which applies analogously to FIG. 4.

Figure 5:
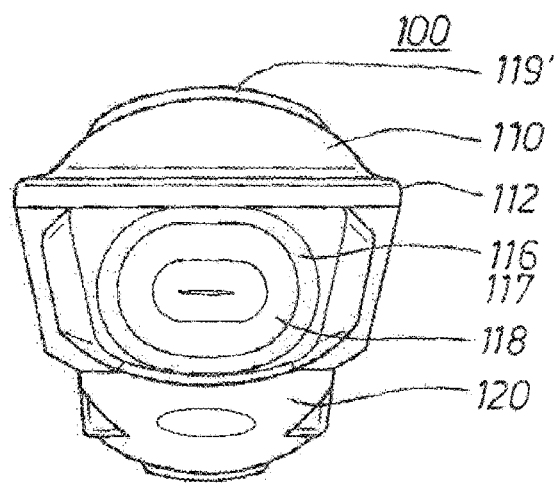
FIGS. 5a to 5d show the separator with the membrane according to a third embodiment and an alternative design of the sealing edge.
Figure 5:
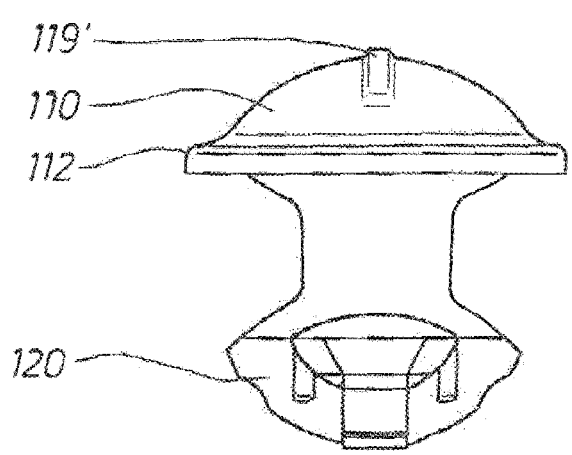
Figure 5:
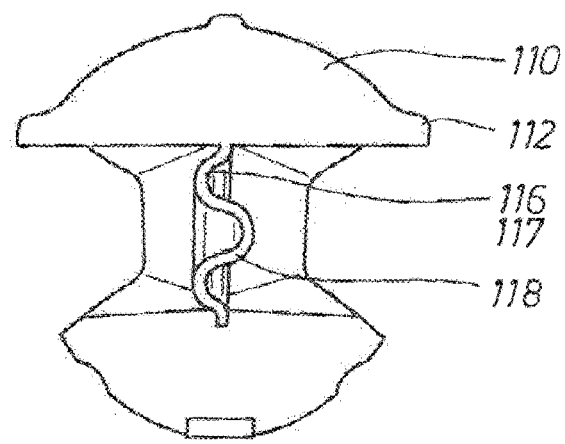
Figure 5:
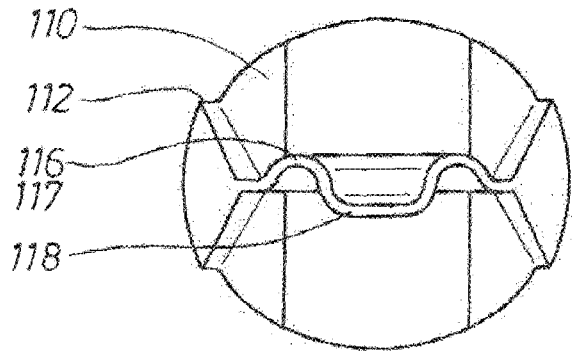

FIG. 5 shows the separator 100 according to the invention in a further embodiment. Unlike in FIGS. 1 and 3, here the float 110 is cup-shaped. FIGS. 5a and 5b show the cup-shaped separator in each case in different side views. FIGS. 5c and 5d show the cup-shaped separator in each case in different sectional views. The wave crests 117 and the wave troughs 118 of the membrane 116 are here also annular, but oval (3rd variant). Furthermore, the sealing edge 112, as shown in the side views according to FIGS. 5a and 5b, is formed in a straight horizontal line.

Figure 6:
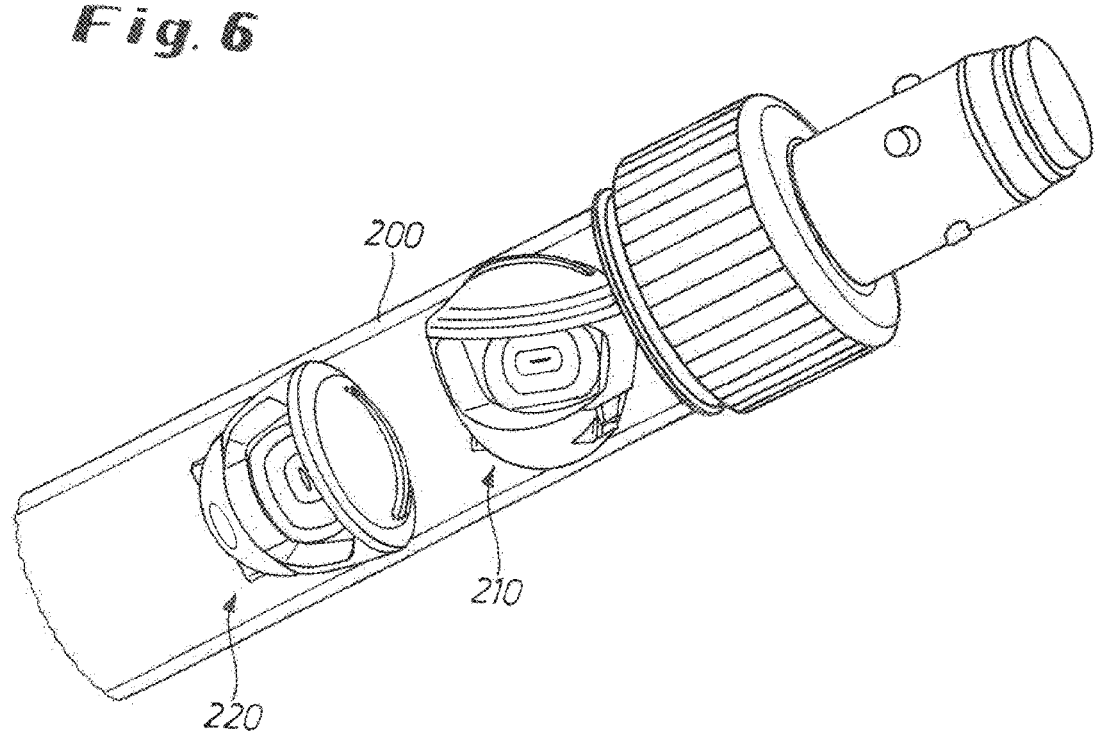
FIG. 6 shows the separator of FIG. 5 in the tubular container.

The description of FIG. 4 in conjunction with the description of FIG. 2 analogously applies to FIG. 6.

The disclosure of the description is not limited to the described embodiments. Rather, in particular, the described alternative embodiments of the membrane, the sealing edge and the float with flattenings or elevations can be combined with each other in any combination.

LIST OF REFERENCE NUMBERS 100 separator
110 float
112 sealing edge
114 constriction
116 membrane
117 wave crest of the membrane
118 wave trough of the membrane
119' local elevation
119" local flattening
120 ballast
200 tubular container
210 initial situation or delivery condition
220 sealing position
230 Intake
K cruor
R circumferential direction
S serum

The invention claimed is:

1. A separator (100) for separating a first phase from a second phase of a liquid under centrifugal force in a tubular container (200), comprising:
a float (110) made of elastic material having a circumferential sealing edge (112) for sealing engagement with the inside of the tubular container (200) when the separator (100) is in a sealing position (220); and
at least one ballast (120) attached to an underside of the float (110),
wherein a density of the ballast (120) is greater than a density of the float (110),
wherein a density of the separator (100) is in a value range between a density of the first phase and a density of the second phase of the liquid, and
wherein the float has a local constriction (114) that is formed as a spring-effect exhibiting membrane (116) surrounded by an outer periphery of the float and configured to seal the float in an area of the constriction against the flow of liquid therethrough.

2. The separator (100) according to claim 1, wherein the liquid is blood, the first phase is blood serum and the second phase is cruor.

3. The separator (100) according to claim 1, wherein the membrane (116) is elastic.

4. The separator (100) according to claim 1, wherein the membrane (116) is wave-shaped with wave crests (117) and wave troughs (118).

5. The separator (100) according to claim 4, wherein the wave crests (117) and the wave troughs (118) of the membrane (116) are annular.

6. The separator (100) according to claim 4, wherein the wave troughs (118) and the wave crests (117) of the membrane (116) extend straight and parallel to one another.

7. The separator (100) according to claim 1, wherein the membrane (116) is made of the same material as the float (110).

8. The separator (100) according to claim 7, wherein the membrane (116) is formed as one piece with the float (110).

9. The separator (100) according to claim 1, wherein that the float (110) is spherical or cup-shaped.

10. The separator (100) according to claim 9, wherein the float (100) has a local elevation (119') or a local flattening (119") on its upper surface facing away from the ballast (120).

11. The separator (100) according to claim 1, wherein the sealing edge (112), viewed in a side view, is wave-shaped in a circumferential direction (R) and at least partially extends around an edge of the constriction (114).

12. The separator (100) according to claim 1, wherein the circumferential sealing edge (112), viewed in a side view, is straight.

13. The separator (100) according to claim 12, wherein the circumferential sealing edge (112), viewed in a side view, extends horizontally.

14. The separator (100) according to claim 1, wherein the ballast (120) is made of a material which is less elastic than a material of the float (110) or a material of the membrane (116).

15. The separator (100) according to claim 1, wherein the membrane extends from one side of the float to an opposite side of the float below the sealing edge to the ballast.

16. The separator (100) according to claim 1, wherein the separator is configured to rotate by 90° between an initial position and the sealing position.

17. The separator (100) according to claim 16, wherein the membrane prevents the liquid from flowing through the separator when the separator is in the initial position.

18. The separator (100) according to claim 1, wherein the membrane is formed as one piece with the float.

\* \* \* \* \*